(12) United States Patent
Genest

(10) Patent No.: US 6,549,639 B1
(45) Date of Patent: Apr. 15, 2003

(54) BODY PART IMAGING SYSTEM

(75) Inventor: Leonard J. Genest, Santa Ana, CA (US)

(73) Assignee: Genovation Inc., Irvine, CA (US)

( * ) Notice: Subject to any disclaimer, the term of this patent is extended or adjusted under 35 U.S.C. 154(b) by 0 days.

(21) Appl. No.: 09/562,842

(22) Filed: May 1, 2000

(51) Int. Cl.[7] .................................. G06K 9/00
(52) U.S. Cl. ........................ 382/100; 382/285
(58) Field of Search ........................ 382/100, 106, 382/199, 194, 203, 154, 285, 286; 600/592; 33/3 R, 4, 5, 3 C

(56) References Cited

U.S. PATENT DOCUMENTS 5,753,931 A * 5/1998 Borchers et al. ............ 600/592
6,029,358 A * 2/2000 Mathiasmeier et al. ....... 33/3 R
6,289,107 B1 * 9/2001 Borchers et al. ............ 382/100

* cited by examiner

Primary Examiner—Phuoc Tran
(74) Attorney, Agent, or Firm—Derrick Michael Reid

(57) ABSTRACT

An imaging system places an object upon a background pattern of regular repetitive marks and records a 2D image that is then processed for determining where in the image the repetitive marks are interrupted by the object, thereby indirectly determining the edge of the object. Multiple 2D images from different perspective are used to create a 3D image of the object. When the object is a human foot, individual bar codes and imaged foot dimensions can be cross-referenced to manufactured shoe sizes for accurate ordering of correctly sized footwear.

19 Claims, 4 Drawing Sheets

SIDE VIEW OF FOOT MEASUREMENT SYSTEM

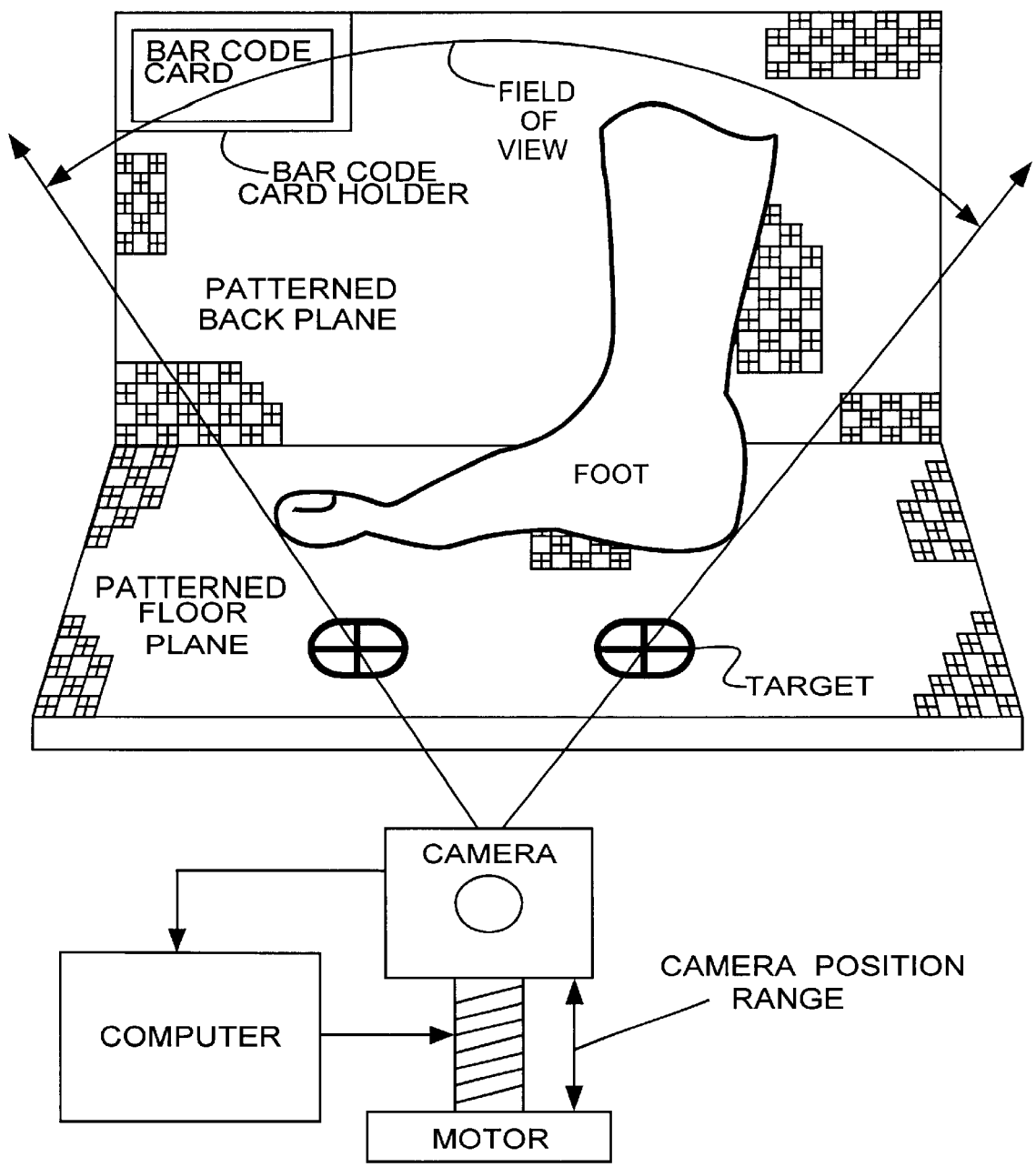
FIG. 1 SIDE VIEW OF FOOT MEASUREMENT SYSTEM

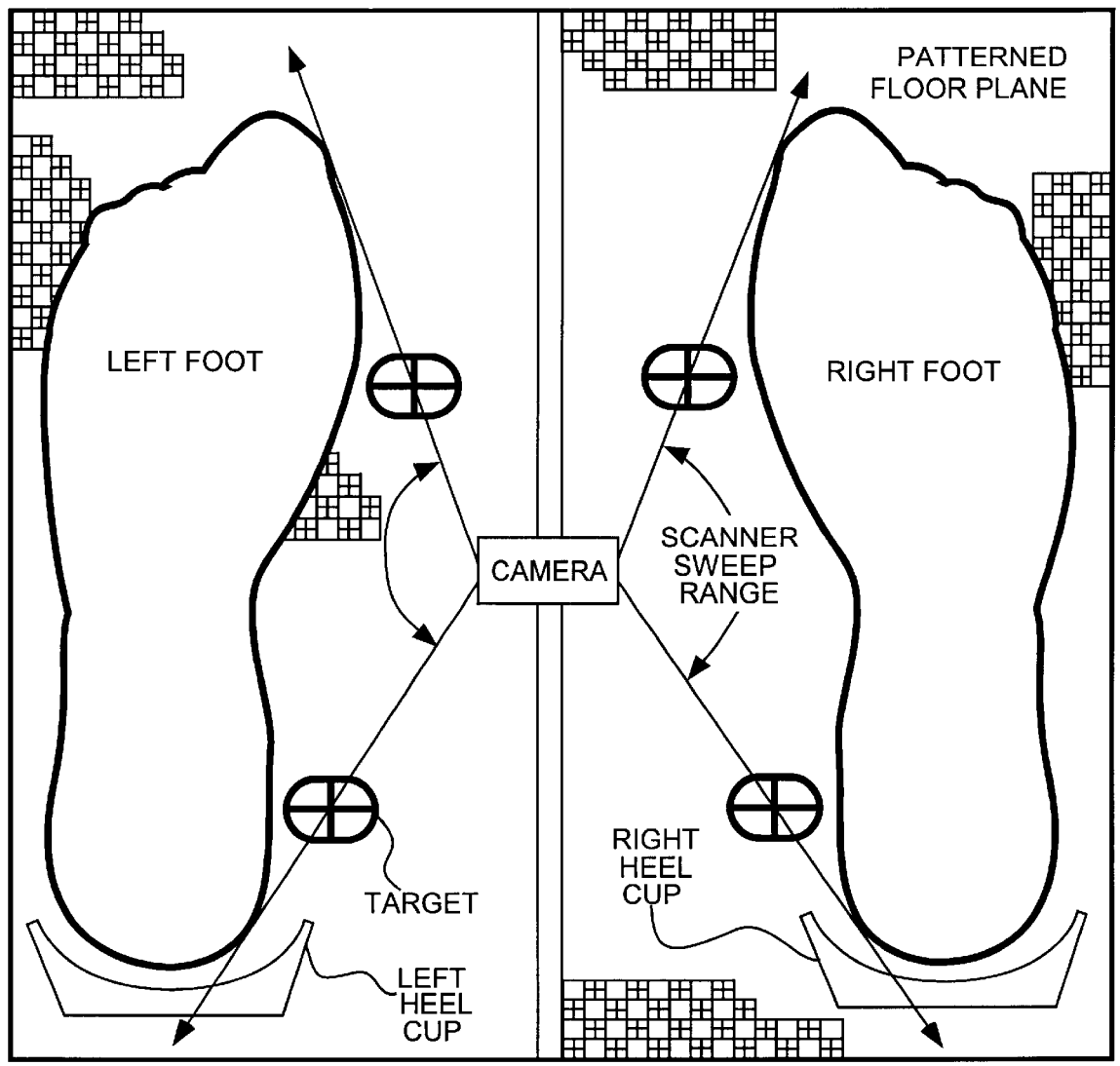
FIG. 2 TOP VIEW OF FOOT MEASUREMENT SYSTEM

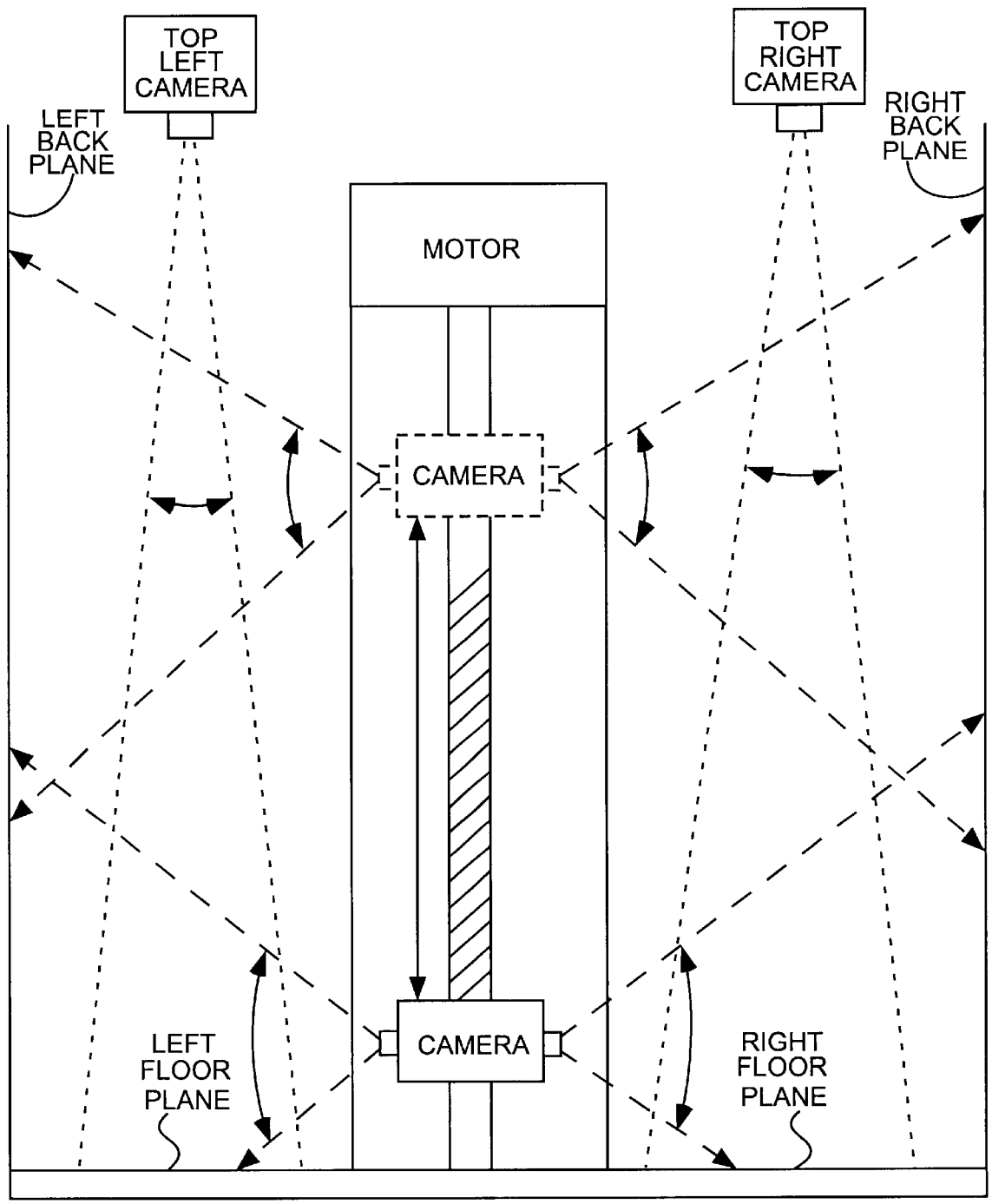
FIG. 3 FRONT VIEW OF FOOT MEASUREMENT SYSTEM

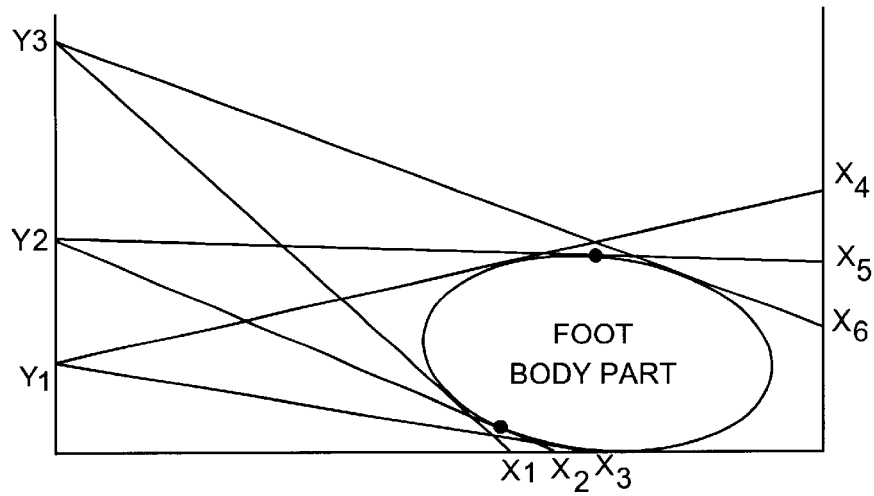
Fig. 4A FOOT TOP AND ARCH SCAN PROCEDURE
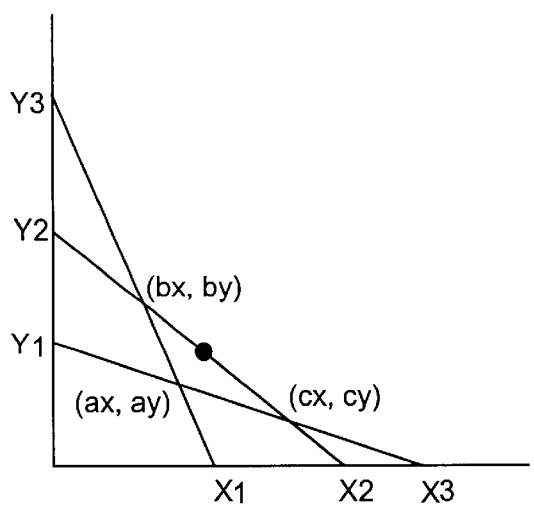
FIG. 4B  FOOT ARCH SCAN GEOMETRY
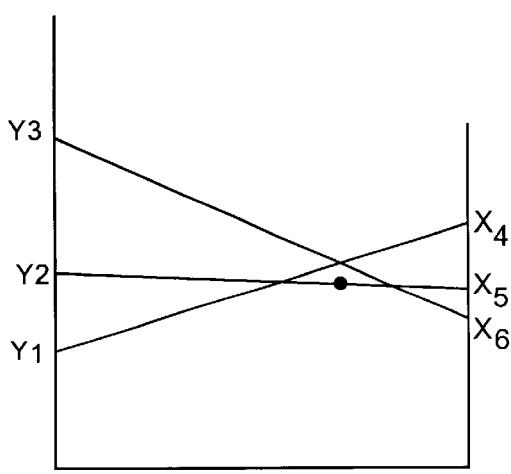
FIG. 4C  FOOT TOP SCAN GEOMETRY

BODY PART IMAGING SYSTEM

REFERENCE TO RELATED APPLICATION

The present application is related to applicant co-pending application entitled "Body Part Imaging Method", filed May 1, 2000, Ser. No. 09/562,843, by the same inventor.

FIELD OF INVENTION

The present invention relates to imaging of human body parts. More particularly, the present invention relates to imaging the edges of a body part or an object, such as a human foot including the footprint, arch and instep using a patterned background.

BACKGROUND OF THE INVENTION

Conventional measurements of 3-D objects have used a laser scanners or area image sensors that scans the area of the object to be imaged. The sensors may be CMOS or charged coupled device (CCD) sensors, such as used in a digital camera. The scanners may be a single line CCD scanner or a PC scanner. Generally, the overall dimensions of an object are measured by imaging the edges of the object. The periphery of the object is constructed when imaging object edges that are contrasted from a different colored background. The edge of the object is interpreted using software algorithms that discerns transitions from the edge of the object from the space behind the object. The space behind the object has to have some degree of color from white to black different from the object so that the data input to an image processing algorithm can indicate the edge of the object. The edges of an object are often blurred or indiscernible from the background as a result of shadowing or the use of similar colors between the background the object. When the object being measured has any edges of a color similar to the background, the algorithm fails to accurately detect the edges, and hence the algorithm inaccurately determines the edges of the object. When the object is multicolored, it is often difficult to accurately discern the edges of the object as the background will merge wit the edges of the object. The inability to accurately detect edges leads to inaccurate sizing of three-dimensional (3D) objects. When contour imaging a 3D object using imaged edges, the scanning or sensing means circumscribes the 3D outline of the object by moving the sensor around the object to image a plurality of edges around the object. The 3D image of the object then constructed will be made up of the continuous outside dimensions of the object and will accurately display the outermost dimensional contour of the object.

Other methods of imaging 3D objects include laser imaging methods that measured the depth of laser projected light beams as the beams are reflected back to a detector using beam deformation and position changes to image depth. Typically, the detector used with the laser detects the position of the laser beam over the entire surface of the object as the laser beam is moved. The laser imaging method often fails due to color, texture and reflection of the imaging laser beam. In both scanning and laser methods, the software algorithms are complex because the imaging process requires scanning and detecting areas of objects having light intensity such that the detector means may not be able to definitive discern the edge of the object. To detect the edges, prediction algorithms are used to fill in areas of the object that are imprecisely detected. Typically, the software algorithm is complex and slow and inherently unreliable. These and other disadvantages are solved or reduced using the present invention.

SUMMARY OF THE INVENTION

An object of the invention is to provide a system and method that indirectly images objects by contrasting the object with a predetermined background pattern.

An object of the invention is to provide a system and method that indirectly images objects by contrasting the object with a predetermined background checkerboard grid pattern of alternating white and black colored areas.

Another object of the invention is provide a system and method for cross-referencing human body and body parts dimensions to manufacture apparel sizes for accurately ordering apparel form manufacturers.

Another object of the invention is to provide a means of capturing both the weighted and non-weighted variations of feet to enable the imaging of arch height and type, and the spread of the feet under weight.

The invention is directed to an imaging system and method that indirectly measures an object using a background pattern. An object to be measured is placed in front of a predetermined background grid. Imaging means image the background pattern that is interrupted by the object placed in front of the background pattern. The system and method images the background pattern. When the ordered regularity of the background pattern is interrupted by the object, the edge is accurately determined by counting the number of alternating areas, such as black and white areas, from a known border of the background pattern or from other predetermined fixed reference locations, targets or purposeful irregularities within the background pattern. Software algorithms then determine the overall measurement of the object where the background pattern has been interrupted to indirectly measure the periphery of the object. A plurality of images taken from different perspectives provide accurate 2D peripheral measurements that are combined to provide a 3D measurement of the object being measured.

The imaging means may include an array of light detecting cells such as charged coupled devices (CCD) or complementary metal oxide silicon (CMOS) area sensors. These sensors are commonly used in a digital cameras having appropriate lenses that focus the image to impinge the image over an image area onto the area sensors. The image in digital form can be stored in a processing system such as a personal computer. A computer processing system is used to process the stored image during an imaging process. A plurality of images may be stored for respective different angle positions of the imaging means. Preferably, for each image recorded, the imaging process counts repetitive marks to reconstruct the visible area of the background pattern. The repetitive marks are preferably blocks in rows and columns of alternating black and white blocks of a preferred checkerboard background pattern. The repetitive marks are counted starting from a known edge position usually known as a reference target.

The imaging process processes the stored image by determined the edge of the object relative to interruption in the regularity of the background pattern. An expected error of one or two blocks, that is, the background pattern image tolerance error, can occur depending on the color of the object being imaged contrasted from the color of the background pattern. Each background pattern, area, mark or block, may be as small as is detectable by the sensor means. In the case of a checkerboard pattern imaging a human foot, for example, the block dimension may be only one millimeter and well within sensor and focusing lens capabilities. Conventional edge average smoothing processes maybe be performed during computer image processing to obtain an average edge contour line depicting the edge of the object accurate to plus or minus one block dimension. Each mark or block represents a fixed dimension. Counting the number of marks or blocks from a plurality of reference targets or from fixed patterned borders will enable by imaging processing, a method for determining the dimensions of the object being measured within one mark or block dimension.

The background pattern only needs predetermining contrasting marks for image recognition and processing. Alternating checkerboard blocks is the simplest to make and use as the preferred background pattern. However, there are several other types of background patterns that may be used. For example, Fresnel patterns may be used where each block deflects the light to appear like lighted and unlighted blocks to the sensor means. For another example, a sublighted platform where black blocks are printed on a clear or translucent bottom material so that light emanates upward through the light translucent blocks. The sublighted platform is advantageous because it eliminates top lighting shadows. Other patterns such as circles, rectangles, triangle, hexagons, among many other, could be used as well, for different applications and accuracy considerations.

The accuracy of the imaging process system and method is determined by the area, mark or block size of the background pattern. Each repetitive background pattern mark or block in the chosen background pattern will have a predetermined minimum number of imaged pixels that is greater than one. The sensory means provides an adequate number of pixels to image the marks or blocks in the background pattern. Each mark or block should have at least two pixels per mark or block in the background pattern. The sensor means must accurately detect each individual mark over a field of view (FOV), such as over a predetermined area of the white or black blocks in the checkerboard pattern when no object is placed in front of the background pattern. The FOV determines the lens focusing requirements for the sensor means. The lens focusing of the sensor means and the number of pixels over the FOV area to be measured must be such as to have at least two pixels focused on each colored block. When using more than two pixel per mark or block, the resolution and resulting quality of the process image is enhanced with improved resolution.

When an object of any color or pattern is placed within the checkerboard area, the imaging means detects an interference in the order of repetitive marks of the background pattern. In the case of a checkerboard background pattern, the regularity of the white to black block images are interrupted by the object. Of course, the object should not have a colored pattern the same as the background pattern. A detection tolerance error can occur when the object being imaged has a color pattern that matches the pattern of the background and when the object pattern is perfectly aligned with the background pattern, which is a highly unlikely event. Various background patterns may be used to accommodate the imaging of any arbitrary colored object.

A preferred use of the invention is for sizing a human being, more particularly, human feet for selecting suitably sized footwear and human bodies for selecting suitably sized clothing. In the case of footwear, great care is needed to provide accurate foot measurements and sized shoes, less the person wearing incorrectly sized fitted shoes may be subject to discomfort and even damage and injury to the feet.

The important parts of a foot to be measured are the periphery of the foot, including the length and width of the foot, as seen from the top of the foot over the approximate center of the forefoot, the side view of the instep and the side view of the arch. In the operation of the system and method, the foot is placed on a floor mat that is printed with an alternating checkerboard pattern preferably in black and white one millimeter blocks. As the scanned pixels in the CCD reach the edge of the foot being scanned, the color could be anything and the output of the CCD could be any voltage between zero and full scale, such as five volts. However, the CCD output sensor will still put out a zero or a one depending if the CCD output is greater than or lesser than one half of the full scale, such as 2.5 volts. From an edge border or target of the checkerboard reference to when the edge of the object is indirectly observed, there will be a discontinuity in the regular pattern of blocks imaged in the presence of the edge of the object. The discontinuity is detected by a change in the regular image pattern. The computer process method will scan for discontinuities over the FOV area covering the placement of the foot all the way from the reference target positions of the checkerboard to the edge of the object being imaged. An image map will be compiled and stored in memory indicating each location point of discontinuity. The location points will trace an edge of the image of the foot. Repeated images taken from the sensor means at various relative angles to the foot, are then used to create a 3D image of the foot. Computer processing can convert the 2D images into a single 3D image of the foot.

In this manner, the system and method enables the creation of a 3D image of an object, such as a foot, by sensing the extent of a background pattern within a field of view to create a 2D image at a respective relative angle between the sensor and the object placed on a background pattern. The processing method indirectly determines the edge of the object on the background pattern at pixel locations relative to one or more reference targets to where the regular background pattern is interrupted by the object. The processing method converts the 2D image of the interrupted background pattern into a 2D edge image of the object. Multiple 2D edge images taken from different perspectives are combined together to create a 3D image of the object. During imaging of a foot, a unique bar code associated with the object being imaged is placed within the FOV and is imaged by the same sensor so as to associate a bar code with the image foot.

Once a body part, such as a foot, has been imaged by scanning and then dimensioned by computer processes imaged into precise foot dimensions including the top of the foot periphery, arch and instep, the foot dimensions are crossed referenced to the bar code for identifying the individual of the foot that was imaged. The foot dimensions can then be cross-referenced to the inside dimensions of footwear styles sold by various footwear manufactures. An individual then need only provide a retailer with an identification of the bar code card. Retail processing methods can then cross reference the bar code card and corresponding bar code to the imaged foot dimensions that are in turn cross referenced to the correct footwear size so that a customer can be provided with the best fitting footwear size produced by the footwear manufacturer, thereby, improving the footwear procurement process eliminating to a large extent returns of footwear due to incorrect sizing. These and other advantages will become more apparent from the following detailed description of the preferred embodiment.

BRIEF DESCRIPTION OF THE DRAWINGS

FIG. 1 depicts a side view of a human foot inserted into a measurement system.

FIG. 2 depicts a top view of two human feet inserted into a measurement system.

FIG. 3 depicts a front view of the measurement system.

FIG. 4A depicts foot top and arch scanning procedure geometry.

FIG. 4B depicts foot arch scanning geometry.

FIG. 4C depicts foot top scanning geometry.

DETAILED DESCRIPTION OF THE PREFERRED EMBODIMENT

An embodiment of the invention is described with reference to the figures using reference designations as shown in the figures. Referring to FIG. 1, a human foot as shown is disposed on a patterned floor plane and in front on a patterned back plane. The patterned floor plane and back plane have, in the preferred form, a checkerboard print, only part of which is shown for convenience, but the print preferably extends over a field of view (FOV) of a camera. The checkerboard print is partially shown for convenience to be alternative square block of white and cross hair blocks, the later of which is actually printed as solid blocks. The field of view angularly extends from the focusing camera so as to capture in the FOV the human foot features desired to be imaged. The patterned print of the background plane and the floor plane extends throughout the FOV. Targets are used to provide relative reference points to the checkerboard prints so as to reference displacement of the human foot relative to the blocks of the checkerboard print. The camera focuses upon the checkerboard pattern to image the foot and the checkerboard print area to capture the FOV image. The camera provides a digital image to a computer processing means that processes the digital image. The image is captured by the camera as a two-dimensional (2D) image containing the reference target points, and the checkerboard of alternating blocks having patterned regularity that is interrupted by the presence of the human foot. The computer is further used to control the position of the camera through a camera position range by actuating a motor so as to capture a plurality of desired 2D images at differing focusing angular views. The computer processes the plurality of captured 2D images into a 3D image of the outermost periphery of the foot resulting in outermost 3D dimensions of the human foot. A bar code identification card is disposed within a bar code cardholder also position within the camera FOV. The bar code of the bard code card is a code that uniquely identifies the human foot to a particular human being so that the computer processes can cross reference the particular human being to the respective 3D image and the resulting 3D dimensions of the foot. The computer can further store data cross referencing shoe sizes of a particular shoe manufacturer to the 3D dimensions of the 3D image so that the computer can determine the appropriate shoe size of the particular manufacturer for the particular feet of the particular human being. By cross-referencing the identification card to the bar code to the peripheral size and shape of the measured foot to the inside cavity dimensions and shape of the footwear.

Referring to FIGS. 1, 2, and 3, and more particularly to FIGS. 2 and 3, an alternative dual imaging embodiment may be used to concurrently capture 2D images of a pair of human feet, a left foot and a right foot. The two feet are disposed on a double patterned floor plane with the camera capturing a pair of respective 2D images for the respective feet. As shown, there is a single camera traversing the vertical range, having two FOVs extending horizontal. The camera captures left and right images through two respective left and right FOVs. The camera can be a single camera that views from one perspective FOV then is pivoted 180 degrees or two cameras vertically translated by the motor in tandem to view both perspective FOV at the same time. The camera and the patterned floor and back planes function in combination as a scanning mechanisms that in effect scans through scanner sweep ranges that are FOVs of the camera. The patterned floor plane is divided into respective left and right halves, each having a respective pair of referencing targets. Vertically extending and opposing left and right backplanes are used to image the vertical height features of the respective human feet. The vertically extending back planes also contain targets, not shown. All of the targets are used to provide reference points for referencing the positions of the blocks within the planes to a known location in advance of imaging. The bi-directional imaging camera is shown to traverse the vertical camera position range. Left and right top cameras are shown to have FOVs extending downward towards the respective pattern floor plane halves to image the outside periphery of the respective feet, and more particularly the forefoot of the feet extending towards and to almost the heel. The heels of the respective feet are shown to be disposed in respective heels cups for proper positioning of the feet on the respective patterned floor planes halves.

The camera may be an exemplar charged-coupled-device (CCD) sensor imaging means used to capture a 2D image and output the captured image in digital form. The image is captured preferably through the sequential scanning of CCD detectors. Conventional CCD cameras may be used for imaging in the preferred form. The image comprising the subject foot and background checkerboards is focused by a lens of the camera onto a silicon chip CCD X-Y array of light detectors representing respective X-Y pixels. A CCD controller of the camera raster-scans the X-Y detectors. When each pixel detector is scanned, an analog value of the light intensity is provided and represents the light intensity for a respective pixel at a particular X-Y coordinate in the X-Y area. The CCD imaging means is fed a clock pulse that advances through each pixel detector by row and by column in a raster scan so that an output of the CCD sensor is provided for each pixel by row and by column, serially, one at a time, until sequencing through all the pixels of the captured image.

The camera captures the black or white blocks of the checkerboard as well as the imaged foot. Each block is captured as two or more pixels having the same substantial output analog value. During image area capturing, the camera generates an analog value of the returned light for each pixel. In the preferred form, monochrome gray-scale image processing is used. For simplicity in constructing a body contour, the white of black imaging through gray-scale conversion is suitable, though other color schemes could be used as well. An analog output for the CCD sensor has a dynamic range between zero and full scale, such as five volts, for spanning the gray-scale values between black to gray-scale values to white. The output of the CCD sensor may be coupled to level detector, not shown, that is set to one half of the full scale value, such as 2.5 volts, for digitizing the CCD gray-scale analog output into a data stream of zero and one bits for computer image processing. Anytime a pixel is sensed from below medium gray to black, the output of the comparator would be below the one half of full scale and the pixel would be digitized a zero bit, and, anytime a pixel is sensed from medium gray to white, the output of the comparator would be detected above 2.5 volts and the pixel would be digitized as a one bit. When the CCD sensor includes an analog to digital converter (DAC), such as an 8 bit DAC, then the most significant bit of the DAC output would be the center value of the gray-scale and this most significant bit is the digitized zero or one bit output to the computer processing means. Even though a CCD with a DAC built on-board provides digital outputs representing the whole dynamic range of the output intensity sensed, only the halfway point is needed to discern an edge of an object. Yet, the computer image processing could process a multiple bit output of the gray scale or color scale for enhanced image processing. In the preferred form, only edge detection is required and only zero and one digital bit intensity resolution is required.

Imaging processing operates upon pixel digitization. Each white or black block of the checkerboard pattern is processed by sensing at least four pixels, two pixel in each of the X rows and Y columns. Along each row or column, each block on the checkerboard is determined by at least two pixels having the same value. A corresponding digital pulse train from the camera is provided to the image processing computer during the raster scan of the image. The pulse train provides a sequence of transitions that occur every block transition when transiting between black and white blocks. The pixel pulse train would include transition levels of alternating zero and one values along each column and row of the captured image, and the computer processing can recognize the pattern of transitions in the pulse train to determine which receive transition corresponds to which image block. The length between the transitions indicates the number of like zero or one digitized pixels. A limited amount of variations in pulse widths between transition for each block includes an inherent tolerance of +/−one pixel. Each block of the checkerboard pattern is not imaged at a perfect right angle, and hence the detected image will naturally have a progression in the number of pixels per block across the rows and across the columns. The checkerboard pattern and the resulting captured image will provide a progressive number of pixels per blocks greater than two pixels per block to cause the progression of pixels per block to vary in a progressive manner. The progression of the number of pixels per block may cover a large range across the entire row or column of the captured image. For example, in the case of the floor checkerboard pattern, in the near field, at one extreme, the number of pixels per blocks may be three, and in the far field, at another extreme, the number of pixels per blocks may be seven, with the number of pixels per blocks progressively increasing from the near field to the far field along a column or row of pixels. For another example, in the case of the back plane checkerboard pattern, or in the case of the floor checkerboard panel imaged by an over head camera, from a center located block, the range number of pixels per block may be at minimum, such as three pixels per block, progressively increasing towards blocks located at the edge of the checkerboard. Computer image processing can detect regular block pixel lengths, and can determine the progression in block pixel lengths. For example, a series of transitions of three pixels per blocks followed by a series of transitions of four pixels per blocks, indicates a natural progressive increase in the number of pixels per block, and would not thereby indicate an interruption of the pixelized image of the checkerboard. The computer image processing can recognize when the block pixel lengths have increase or decreased in a progressive manner across rows and columns of the captured image.

When a transition from a first block pixel length is followed by a transition of a second block pixel length, the change should be within the +/−one pixel tolerance, allowing for the average progressive change in the block pixel length through a row and column. The error in digitization is at least +/−one pixel accounting for the edge of block. The +/−one pixel error can be compensated for by smoothing to provide an enhanced contour image. The +/−one pixel errors tend to render the object smaller then the actual size because the interruption will occur after the edge is encountered when scanning the checkerboard blocks towards the foot edge. The block error that can be tolerated and compensated through smoothing is typically twice the block size. The average block error can be partially compensated by subtracting one block from the block count to the encountered edge. When a change in block pixel length, that is the pixel duration between transitions, exceeds the +/−one pixel tolerance, the computer image processing can recognize this abrupt change as an interruption in the progressive block pixel length. The computer processes can detect this abrupt change in the transition period indicating an interruption in the progression of the block pixel length so as to then indicate and determine when the checkerboard pattern has been interrupted by the presence of the body part being imaged. Hence, each block is digitized into a number of pixels per block for each square block, and this number progressively increases or decreases across rows and columns in the FOV. Each block is positioned at a predetermined distance from the checkerboard pattern target. The checkerboard target preferably has a unique pixel definition, such as a very large square block, recognized as such by the image processing computer. The target can be replaced by simple edge checkerboard detection, by referencing the start of the checkerboard pattern at the edge of the checkerboard. The checkerboard edge then providing a reference point, as does the target, to the remaining blocks for block position count determination. Block position count determination is achieved by counting the number of the blocks from the reference point, be it a special target or a checkerboard edge, or other suitable image reference. Hence, the image processing computer receives the pixel pulse train and determines, while counting the blocks in both the rows and columns, at what X-Y block position in the checkerboard the block pixel length has been abruptly interrupted, thereby providing an X-Y block interruption position indicating a detected edge of the imaged foot. When the order of alternative blocks, that is, the order of alternating transitions of a number of pixels per block +/−one pixel is disrupted, this disruption indicates that the foot edge interrupts the image of the checkerboard pattern. The disruption in the predetermined order of transitions is recognized as an abrupt interruption of the image of the alternating white and black blocks of alternating transition of the number of pixels per block +/−one pixel. The disruptions of the foot edge appear as truncated or extended number of pixels of the alternating transition. For example, a transition between one to three pixels in duration, in the two pixels per block range, indicates an abrupt interruption of the transition pulse train, and thereby indicating an abrupt interruption of the image checkerboard pattern by the presence of the edge of the human foot. The image processing computer determines the interruption location along each row and column of the checkerboard for each 2D image. With multiple 2D images, the computer processes can indirectly determines the periphery of the imaged human foot disposed in front of the checkerboard.

Referring to all of the Figures, and more particularly to FIGS. 4A, 4B and 4C, the vertically traversing imaging camera capture images at various vertical positions to generate multiple 2D images. As indicated in FIGS. 4A, 4B and 4C, the vertical imaging camera captures images at various vertical positions, Y1, Y2 and Y3. The captured images include the checkerboard patterned of the floor and black planes. The checkerboard pattern is interrupted by the presence of the foot at respective block positions. In FIG. 4A, for vertical camera positions Y1, Y2, and Y3, the floor plane checkerboard pattern is interrupted at X1, X2, and X3 horizontal floor plane block positions, respectively, and the back plane checkerboard pattern is interrupted at X4, X5 and X6 vertical back plane block positions, respectively.

To measure the outside periphery of a foot as viewed from the top of the forefoot, the top left and right cameras are used in the over head above the forefoot about midway between the toe and the front of the leg for the longest foot expected to ever be measured when the foot is against the back heel-cup. The FOV of the over head camera would then cover as far back to the heel as possible, adequate to measure the forefoot of the shortest foot to be measured. The heel cup could be moved slidably forward for very small feet into the FOV of the over head camera. The over head camera does not measure the heel periphery because the ankle and leg will shadow the hell cup, but additional cameras could be used to image the heel if desired. The important part of the foot to image is the part of the forefoot in front of the ankle.

To image the side of the foot to capture the outline of the instep requires that the camera be placed on the medial side of the foot and with a back plane of the checkerboard pattern extending vertically on the lateral side of the foot. The foot instep is disposed at a particular gap distance from the vertical checkerboard back plane while the camera is vertically positioned at a particular elevation for each capture 2D image. Various instep heights will not be accurately measured by a single 2D image because of angular position errors resulting from differing foot gap distances and at a particular camera elevation. Because the instep height of the feet will significantly vary for different feet, it is necessary to compensate for the angular error. Elevating the camera by motor control to varying elevations enable the capturing of multiple 2D images to adequately image the instep. When the camera takes multiple 2D images at respective multiple vertical heights, the number of pattern row and column blocks counted down from the top will change. Through triangulation computer processing, the actual height of the instep can be calculated from the plurality of 2D images. The more 2D images taken, the more accurately the instep height calculation will be.

The arch height on the medial side of the foot is an important arch dimension used to build an arch support. The arch height can be imaged by the camera taking the plurality of 2D images. By positioning the camera with reference to the floor at various elevations, and taking multiple images of the arch area, the camera will image the floor plane checkerboard pattern at various respective angles. The floor plane checkerboard pattern is imaged to the extend not blocked by the presence of the foot. The presence of the foot will interrupt the regularity of the imaged background pattern blocks. The arch height and position of the foot determines the extend of uninterrupted checkerboard pattern imaging. The higher the arch of the foot is, the more checkerboard blocks will be counted under the arch from the target position. To adequately determine the contour of the arch, the camera is moved incrementally vertically while taking multiple 2D images. As the camera moves upward, fewer floor plane horizontal blocks will be counted because the rising arch will interrupt imaging of the floor plane blocks in varying amounts. The digitized 2D image information is fed to the image processing computer that in turn calculates the arch height and approximate configuration shape by performing a series of triangulation calculations. As the vertical position of the camera is increased, the number of horizontal floor blocks counted is decreased because of the interruption of the captured image by the presence of the foot. At the lowest Y1 camera position, the farthest position under the arch will be seen at the largest number of blocks imaged and counted. In the exemplar form, when the camera is positioned at the Y1 elevation, the value that represents the lowest line of sight is the Y1,X3 line that relates to the largest number of horizontal blocks from the camera to the X3 position at Y1 number of blocks in elevation. The number of horizontal blocks can be determined from the number of horizontal blocks from the reference point that is in turn at a predetermined number of horizontal blocks from the camera. This means that X1 number of horizontal blocks is seen under the foot when the camera is at the Y1 vertical position of Y1 number of blocks high. The horizontal values of X blocks for other lines of sight at respective camera elevations can be also determined during imaging. With three captured images at respective increasing vertical positions, a virtual imaging triangle is create for triangulation computation purposes providing three intersecting points designated (ax,ay), (bx,by), and (cx,cy). The segment between (bx,by) and (cx,cy) forms the hypotenuse of a virtual triangle having a center point that is the closest approximation of the actual contour point on the arch which is determined to be the edge location. By moving the camera along the vertical dimension, additional virtual lines can be create and additional virtual triangles can be created, the center of each hypotenuse representing the closest approximation contour points of the edge of the rising arch as viewed from the vertical position. More than three images provide center points that will describe the contour of the arch along a cross section of the foot for constructing the 3-D image and dimensions of the arch.

It may now be apparent that the same triangulation calculation method can be used to describe the instep of the foot. The difference being that in instead of counting the blocks on the floor plane checkerboard pattern, the camera focuses on the vertical back plane checkerboard pattern on the lateral side of the foot where the foot is positioned between the camera and the vertical back plane. The processing requires that the vertical height position of the camera positional range exceed the highest instep height. The higher the camera can be moved with reference to the highest part of the instep determines the amount of the lateral side of foot that can be seen by the camera and hence how far down the lateral side of the foot can be measured. By using this imaging method, it is possible to describe the top of the instep at any longitudinal block position between the toe and the heel as an arc over the top of the instep where the peak position of the arc is known with relation to the lateral and medial sides of the foot. The general outside shape of the leading and falling sides of the arc are discernable and calculable within the angle of the FOV of the camera.

While the preferred embodiment is directed towards imaging a foot, the same method can be applied to imaging an entire human body, or any arbitrary object. For full body imaging, a larger vertical plane of checkerboard pattern is used. The camera views a section of area at a time depending on the number of pixels in the CCD camera and the focused FOV. The size of the section is determined by the size of the checkerboard blocks and the number of pixels per block. Because the body will be some distance from the vertical checkerboard plane, the camera will need to assume several locations both horizontal and vertical so that the same method of triangulation calculation can be used to produce the curved edges of the human body being measured. A group of two sets of images may be taken, for example, a first set of images are of the back of the person with the back of the person facing the camera, and a second set of images are of the side of a person with the side of the person facing the camera. This group of images would provide 2D image information to reconstruct the 3D profile of a person. To expedite imaging, at increase costs, a plurality of cameras could be placed vertically and staggered from each other so that all of the cameras move in unison when actuating the motor. The cameras could be driven by another motor that moves the camera in the same plane as the checkerboard back plane from one side to the other such as left side to and from to right side. As the cameras move from one side to the other, the body will block the checkerboard pattern at various amounts depending on the line of sight, and the triangulation calculation would produce the body contour image. More than one camera may be used along the vertical direction to cover the full height of a tall person. The person may be sectioned into elevation bands wherein a plurality of images is taken. The number of bands is determined by the size of the checkerboard blocks and the number of pixels imaged in each block. The person being imaged may further stand on a rotating platform that rotates the vertical axis of the person so that for each stop position of the platform, the camera/s perform a sweep to capture the the number of blocks hidden by the shadow of the body of the periphery of the body. The peripheries at a number of rotational positions are thus measured and recorded to build a series of dimensions for a number of elevation on the body and for a multiplicity of points around the body. The computer can then use best curve fitting algorithms to smooth between the points to produce a full body 3-D image with accurate dimensions. For full body scanning, the person would modestly wear snug fitting clothes to display the actual body contours.

In may further be apparent, that other imaging system configurations could be used to take advantage of indirect imaging processing using the background checkerboard pattern. Furthermore, the block could be rectangles or other shapes to meet desired accuracy in each X-Y dimension. The camera could be replaced with a single line CCD sensor such as a typical desk scanner and then moved across bands as scanned line images sequentially. The checkerboard pattern could be replaced with a wall of checkerboard physical bumps that would enable a laser to scan the physical checkerboard pattern as sequential group of regular depth changes interrupted by the edge of the object when the transition ordered sequence is abruptly interrupted. The laser would be moved or the laser beam deflected across bands of imaged lines.

Each foot can be imaged, one foot at a time to reduce the number of camera used and checkerboard required. Suitable lighting means is used to reduce shadows to provide equal and adequate imaging of all of the blocks on the checkerboard. The blocks could be colors other then just black and white, to provide enhanced calculated positions without the use of a target. The interruptions could be computed from the edge of the checkerboard rather that from the target so that the target is not used, but in either case, a relative reference point is needed to determine the distance from a known point to the point of image interruption. Overprinted colors could be used to increase resolution or improve the edge detection depending on the color and physical configuration of the object to measure. The camera movement is preferably linear for simplicity, however, moving the elements in an arc that somewhat follows the contour of the object to be measured could be used for enhanced resolution and increased area coverage. The regular pattern of the checkerboard squares may be progressively dimensioned to compensate for the progression in angular error with the distance from the lens so that all of the resulting transition outputs have the same number of pixels per blocks. The checkerboard could also incorporate specific pattern interruptions that are sensed by the computer as targets for position accuracy check or other detection or verification reasons. Such purposeful interruptions could be used to calibrate the camera field and pixel organization or linearity.

Without a foot in place, the camera can observe all of the alternating blocks across the entire FOV. The camera can be used to check the cleanliness of the checkerboard pattern and then for use for calibration of the light intensity for readjusting the medium gray-scale point that differentiates white from black blocks. When the checkerboard is soiled by dirt or body oils, the orderly. progressive sequence of blocks could be interrupted thus indicating that the pad needs to be cleaned during calibration testing. For compensation during use prior to cleaning, the light intensity may be increased to compensate for the reduction in white block reflection due to being soiled when it becomes slightly less then pure white.

To properly adjust the light source to optimize the sensor detection and to compensate for light source variations due to power fluctuations and bulb life and to some degree to compensate for the cleanliness of the imaging checkerboard pattern, each sensor FOV which also includes a light source to illuminate the FOV includes a series of increasing gray density blocks in a specified location not ever covered by the object being measured. The light reflected from the different gray density blocks is proportional to the intensity of the light source. The power applied to the light source is controlled by a light dimmer controlled by the computer which in turn receives light intensity values from the camera for the blocks in question. The dimmer controls the power applied to the light bulb so that the intensity is adjusted to provide a zero or one output for a specified pair of gray density blocks. This light adjustment is then used for the balance of the measurement session. This assures that the light level is accurately controlled at all time.

As may now be apparent, the imaging system can be used to image any arbitrary object other than human feet or body part, as long as the object interrupts the imaged background pattern. Those skilled in the art can make enhancements, improvements, and modifications to the invention, and these enhancements, improvements, and modifications may nonetheless fall within the spirit and scope of the following claims.

What is claimed is:

1. A system for imaging an object, the system comprising,
a surface having patterned areas and a reference area, the object providing a object image, the object being disposed in front of patterned areas for obstructing patterned images of the patterned areas positioned relative to the reference area providing an unobstructed reference image,
a camera for focusing upon the object, upon the patterned areas, and upon the reference areas from differing perspectives at respective perspective positions for capturing respective composite images each comprising the object image, the patterned images and the reference image, the camera for providing a data stream of the composite image comprising X rows and Y columns of an array of pixels, the data stream providing a series of transitions indicating regularity of the patterned images, the duration of between each transition indicating a number of pixels along one of the X rows and Y columns of the array of pixels, and a processing means for receiving the data stream and for determining along one of the rows or columns of the array of pixels the number of pixels between each of the transitions for determining an interruption in regularity of number of pixels between each of the transitions for indicating where the object obstructs the patterned areas at an obstructed pattern area of one of the patterned areas for indirectly indicating the 2D edge point of the object, and for determining a distance between the reference area and obstructed patterned area for determining the 2D edge point of the object relative to the reference area.

2. The system of claim 1 wherein, the patterned areas are black and white checkerboard areas.

3. The system of claim 1 wherein the object is a human foot.

4. The system of claim 1 wherein, the camera is further for capturing a plurality of composite images from a respective plurality of positions for providing a respective plurality of data streams, and the processing means is further for determining a respective plurality of 2D edge points.

5. The system of claim 4 wherein the plurality of 2D edge points correlates to a dimension of the object.

6. The system of claim 4 wherein, the processing means is further for computing a 3D edge point of the edge of the object from the plurality of 2D edge points.

7. The system of claim 6 wherein, the 3D edge point is a spatial position relative the reference point.

8. The system of claim 6 wherein, the processing means is further form computing a plurality of 3D edge points from the plurality of 2D edge points.

9. The system of claim 8 wherein the plurality of 3D points correlate to a dimension of the object.

10. The system of claim 8, wherein the object is a foot of a human being and the dimension comprise a foot length, a forefoot height and an arch height.

11. A system for imaging a foot of a human being, the system comprising, a floor panel having floor patterned areas, a back panel having back pattern areas, a reference area, the foot providing a foot image, the foot being disposed in on the floor panel on the floor patterned areas and in front of back panel in front of the back patterned areas for respectively obstructing the floor and back patterned images of the pattern areas positioned relative to the reference area providing an unobstructed reference image, a camera means for focusing upon the foot, upon the floor patterned areas, upon the back patterned areas, and upon the reference areas from differing perspectives at respective perspective positions for capturing respective composite images each comprising the foot image, the floor and back patterned images and the reference image, the camera mean for providing a data stream of the composite image comprising X rows and Y columns of an array of pixels, the data stream providing a series of transitions indicating regularity of the patterned images, the duration of between each transition indicating a number of pixels along one of the X rows and Y columns of the array of pixels, and a processing means for receiving the data stream and for determining along one of the rows or columns of the array of pixels the number of pixels between each of the transitions for determining an interruption in regularity of number of pixels between each of the transitions for indicating where the foot obstructs the floor and back patterned areas at an obstructed pattern area of one of the patterned areas for indirectly indicating the 2D edge point of the object, and for determining a distance between the reference area and obstructed patterned area for determining the 2D edge point of the object relative to the reference area.

12. The system of claim 11 wherein, the floor and back patterned areas are black and white checkerboard areas, and the camera means focuses upon the foot from above the foot obstructing floor patterned areas.

13. The system of claim 11 wherein, the floor and back patterned areas are black and white checkerboard areas, and the camera means focuses upon the foot from beside the foot obstructing floor and back patterned areas.

14. The system of claim 11 wherein, the camera is further for capturing a plurality of composite images from a respective plurality of positions for providing a respective plurality of data streams, and the processing means is further for determining a respective plurality of 2D edge points.

15. The system of claim 14 wherein the plurality of 2D edge points correlates to dimensions of the foot, the dimensions comprising a foot length, a foot width, an arch height, and a forefoot height.

16. The system of claim 14 wherein, the processing means is further for computing a 3D edge point of the edge of the foot from the plurality of 2D edge points.

17. The system of claim 16 wherein, the 3D edge point is a spatial position relative the reference point.

18. The system of claim 16 wherein, the processing means is further form computing a plurality of 3D edge points from the plurality of 2D edge points.

19. The system of claim 18 wherein the plurality of 3D points correlate to dimensions of the foot, the dimensions comprising a foot length, a foot width of the foot, an arch height and a forefoot height.

\* \* \* \* \*